United States Patent
Kahn et al.

(10) Patent No.: US 12,048,529 B1
(45) Date of Patent: *Jul. 30, 2024

(54) HARDWARE SENSOR SYSTEM FOR IMPROVED SLEEP DETECTION

(71) Applicants: Philippe Richard Kahn, Santa Cruz, CA (US); Arthur Kinsolving, Santa Cruz, CA (US); Mark Andrew Christensen, Santa Cruz, CA (US); Mihai Ionescu, Ben Lomond, CA (US); Sean Brooks Harre, Santa Cruz, CA (US); David Vogel, Santa Cruz, CA (US)

(72) Inventors: Philippe Richard Kahn, Santa Cruz, CA (US); Arthur Kinsolving, Santa Cruz, CA (US); Mark Andrew Christensen, Santa Cruz, CA (US); Mihai Ionescu, Ben Lomond, CA (US); Sean Brooks Harre, Santa Cruz, CA (US); David Vogel, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/047,258

(22) Filed: Oct. 17, 2022

Related U.S. Application Data

(63) Continuation of application No. 16/601,561, filed on Oct. 14, 2019, now Pat. No. 11,471,097.
(Continued)

(51) Int. Cl.
*A61B 5/0205* (2006.01)
*A47C 27/08* (2006.01)
(Continued)

(52) U.S. Cl.
CPC .......... *A61B 5/1126* (2013.01); *A47C 27/083* (2013.01); *A61B 5/0205* (2013.01);
(Continued)

(58) Field of Classification Search
CPC ... A61B 5/0205; A61B 5/4809; A61B 5/4812; A61B 5/4815; A61G 7/05
See application file for complete search history.

(56) References Cited

U.S. PATENT DOCUMENTS 2,082,843 A 6/1937 Mathez
3,541,781 A 11/1970 Bloom
(Continued)

FOREIGN PATENT DOCUMENTS

AU 2003203967 A1 11/2004
CH 377738 A 1/1964
(Continued)

OTHER PUBLICATIONS

"NPL—EasySense LTD", archive.org, accessed: Jan. 7, 2019, published: Nov. 27, 2006.
(Continued)

*Primary Examiner* — Lynsey C Eiseman
*Assistant Examiner* — Skylar Lindsey Christianson
(74) *Attorney, Agent, or Firm* — Nicholson De Vos Webster & Elliott LLP; Judith Szepesi

(57) ABSTRACT

A hardware sensor system comprising a piezo sensor outputting charge data corresponding to a motion, an insulated cable from the piezo sensor to a receiver, to transmit the charge data, an insulated charge to voltage converter on the receiver, the insulated charge to voltage converter converting the charge data to voltage data, an analog-to-digital converter to convert the voltage data to digital data, and an uploader to upload the data to a server for processing.

21 Claims, 7 Drawing Sheets

Related U.S. Application Data

(60) Provisional application No. 62/745,976, filed on Oct. 15, 2018, provisional application No. 62/745,984, filed on Oct. 15, 2018, provisional application No. 62/745,978, filed on Oct. 15, 2018.

(51) Int. Cl.
  *A61B 5/00* (2006.01)
  *A61B 5/11* (2006.01)
  *A61G 7/05* (2006.01)

(52) U.S. Cl.
  CPC .......... *A61B 5/1118* (2013.01); *A61B 5/4809* (2013.01); *A61B 5/4812* (2013.01); *A61B 5/4815* (2013.01); *A61B 5/7264* (2013.01); *A61G 7/05* (2013.01)

(56) References Cited

U.S. PATENT DOCUMENTS

| | | | |
|---|---|---|---|
| 3,683,933 A * | 8/1972 | Mansfield | A61N 1/37512 607/36 |
| 3,798,889 A | 3/1974 | Chadwick | |
| 4,228,806 A | 10/1980 | Lidow | |
| 4,297,685 A | 10/1981 | Brainard, II | |
| 4,322,609 A | 3/1982 | Kato | |
| 4,573,804 A | 3/1986 | Kavoussi et al. | |
| 4,788,533 A | 11/1988 | Mequignon | |
| 4,848,360 A | 7/1989 | Palsgard et al. | |
| 4,858,609 A | 8/1989 | Cole | |
| 4,982,738 A | 1/1991 | Griebel | |
| 5,008,865 A | 4/1991 | Shaffer et al. | |
| 5,047,930 A | 9/1991 | Martens et al. | |
| 5,168,759 A | 12/1992 | Bowman | |
| 5,275,159 A | 1/1994 | Griebel | |
| 5,335,657 A | 8/1994 | Terry et al. | |
| 5,458,105 A | 10/1995 | Taylor et al. | |
| 5,545,192 A | 8/1996 | Czeisler et al. | |
| 5,562,106 A | 10/1996 | Heeke et al. | |
| 5,671,733 A | 9/1997 | Raviv et al. | |
| 5,844,996 A | 12/1998 | Enzmann et al. | |
| 5,868,647 A | 2/1999 | Belsole | |
| 5,928,133 A | 7/1999 | Halyak | |
| 5,961,447 A | 10/1999 | Raviv et al. | |
| 6,014,682 A | 1/2000 | Stephen et al. | |
| 6,045,514 A | 4/2000 | Raviv et al. | |
| 6,231,527 B1 | 5/2001 | Sol | |
| 6,239,706 B1 | 5/2001 | Yoshiike et al. | |
| 6,350,275 B1 | 2/2002 | Vreman et al. | |
| 6,361,508 B1 | 3/2002 | Johnson et al. | |
| 6,468,234 B1 | 10/2002 | Van et al. | |
| 6,547,728 B1 | 4/2003 | Cornuejols | |
| 6,556,222 B1 | 4/2003 | Narayanaswami | |
| 6,834,436 B2 | 12/2004 | Townsend et al. | |
| 6,888,779 B2 | 5/2005 | Mollicone et al. | |
| 6,928,031 B1 | 8/2005 | Kanevsky et al. | |
| 6,963,271 B1 | 11/2005 | Fyffe | |
| 7,006,650 B1 | 2/2006 | Wild | |
| 7,041,049 B1 | 5/2006 | Raniere | |
| 7,106,662 B1 | 9/2006 | Acker, Jr. | |
| 7,139,342 B1 * | 11/2006 | Phanse | H04B 3/23 375/350 |
| 7,153,278 B2 | 12/2006 | Ono et al. | |
| 7,280,439 B1 | 10/2007 | Shaddox | |
| 7,366,572 B2 | 4/2008 | Heruth et al. | |
| 7,513,003 B2 | 4/2009 | Mossbeck | |
| 7,559,903 B2 | 7/2009 | Moussavi et al. | |
| 7,572,225 B2 | 8/2009 | Stahmann et al. | |
| 7,652,581 B2 | 1/2010 | Gentry et al. | |
| 7,841,987 B2 | 11/2010 | Sotos et al. | |
| 7,862,226 B2 | 1/2011 | Bracher et al. | |
| 7,868,757 B2 | 1/2011 | Radivojevic et al. | |
| 7,914,468 B2 | 3/2011 | Shalon et al. | |
| 7,974,849 B1 | 7/2011 | Begole et al. | |
| 8,179,270 B2 | 5/2012 | Rai et al. | |
| 8,193,941 B2 | 6/2012 | Wolfe et al. | |
| 8,398,546 B2 | 3/2013 | Pacione et al. | |
| 8,407,835 B1 | 4/2013 | Connor | |
| 8,475,339 B2 | 7/2013 | Hwang et al. | |
| 8,482,418 B1 | 7/2013 | Harman | |
| 8,577,448 B2 | 11/2013 | Bauer et al. | |
| 8,680,974 B2 | 3/2014 | Meiertoberens et al. | |
| 8,738,925 B1 | 5/2014 | Park et al. | |
| 8,892,036 B1 | 11/2014 | Causey et al. | |
| 8,909,357 B2 | 12/2014 | Rawls-Meehan | |
| 8,942,719 B1 | 1/2015 | Hyde et al. | |
| 9,060,735 B2 | 6/2015 | Yang et al. | |
| 9,161,719 B2 | 10/2015 | Tsutsumi et al. | |
| 9,257,029 B1 | 2/2016 | Hendrick et al. | |
| 9,448,536 B1 | 9/2016 | Kahn et al. | |
| 9,474,876 B1 | 10/2016 | Kahn et al. | |
| 9,594,354 B1 | 3/2017 | Kahn et al. | |
| 9,675,268 B2 | 6/2017 | Bauer et al. | |
| 9,844,336 B2 | 12/2017 | Zigel et al. | |
| 10,004,452 B2 | 6/2018 | Kazem-Moussavi et al. | |
| 10,207,075 B1 | 2/2019 | Kahn et al. | |
| 10,252,058 B1 | 4/2019 | Fuerst | |
| 10,335,060 B1 | 7/2019 | Kahn et al. | |
| 10,842,968 B1 | 11/2020 | Kahn et al. | |
| 11,100,922 B1 | 8/2021 | Mutagi et al. | |
| 2001/0049482 A1 | 12/2001 | Pozos et al. | |
| 2002/0080035 A1 | 6/2002 | Youdenko | |
| 2002/0100477 A1 | 8/2002 | Sullivan et al. | |
| 2002/0124848 A1 | 9/2002 | Sullivan et al. | |
| 2003/0095476 A1 | 5/2003 | Mollicone et al. | |
| 2003/0204412 A1 | 10/2003 | Brier | |
| 2003/0227439 A1 | 12/2003 | Lee et al. | |
| 2003/0231495 A1 | 12/2003 | Searfoss | |
| 2004/0034289 A1 | 2/2004 | Teller et al. | |
| 2004/0049132 A1 | 3/2004 | Barron et al. | |
| 2004/0071382 A1 | 4/2004 | Rich et al. | |
| 2004/0111039 A1 | 6/2004 | Minamiura et al. | |
| 2004/0133081 A1 | 7/2004 | Teller et al. | |
| 2004/0210155 A1 | 10/2004 | Takemura et al. | |
| 2004/0218472 A1 | 11/2004 | Narayanaswami et al. | |
| 2005/0012622 A1 | 1/2005 | Sutton | |
| 2005/0043645 A1 | 2/2005 | Ono et al. | |
| 2005/0075116 A1 | 4/2005 | Laird et al. | |
| 2005/0076715 A1 | 4/2005 | Kuklis et al. | |
| 2005/0143617 A1 | 6/2005 | Auphan | |
| 2005/0154330 A1 | 7/2005 | Loree et al. | |
| 2005/0190065 A1 | 9/2005 | Ronnholm | |
| 2005/0236003 A1 | 10/2005 | Meader | |
| 2005/0237479 A1 | 10/2005 | Rose | |
| 2005/0245793 A1 | 11/2005 | Hilton et al. | |
| 2005/0283039 A1 | 12/2005 | Cornel | |
| 2005/0288904 A1 | 12/2005 | Warrior et al. | |
| 2006/0017560 A1 | 1/2006 | Albert | |
| 2006/0025299 A1 | 2/2006 | Miller et al. | |
| 2006/0064037 A1 | 3/2006 | Shalon et al. | |
| 2006/0097884 A1 | 5/2006 | Jang et al. | |
| 2006/0136018 A1 | 6/2006 | Lack et al. | |
| 2006/0150734 A1 | 7/2006 | Mimnagh-Kelleher et al. | |
| 2006/0252999 A1 | 11/2006 | Devaul et al. | |
| 2006/0266356 A1 | 11/2006 | Sotos et al. | |
| 2006/0279428 A1 | 12/2006 | Sato et al. | |
| 2006/0293602 A1 | 12/2006 | Clark | |
| 2006/0293608 A1 | 12/2006 | Rothman et al. | |
| 2007/0016091 A1 | 1/2007 | Butt et al. | |
| 2007/0016095 A1 | 1/2007 | Low et al. | |
| 2007/0093722 A1 | 4/2007 | Noda et al. | |
| 2007/0100666 A1 | 5/2007 | Stivoric et al. | |
| 2007/0129644 A1 | 6/2007 | Richards et al. | |
| 2007/0139362 A1 | 6/2007 | Colton et al. | |
| 2007/0191692 A1 | 8/2007 | Hsu et al. | |
| 2007/0239225 A1 | 10/2007 | Saringer | |
| 2007/0250286 A1 | 10/2007 | Duncan et al. | |
| 2007/0251997 A1 | 11/2007 | Brown et al. | |
| 2007/0287930 A1 | 12/2007 | Sutton | |
| 2008/0062818 A1 | 3/2008 | Plancon et al. | |
| 2008/0109965 A1 | 5/2008 | Mossbeck | |
| 2008/0125820 A1 | 5/2008 | Stahmann et al. | |
| 2008/0169931 A1 | 7/2008 | Gentry et al. | |
| 2008/0191885 A1 | 8/2008 | Loree et al. | |

(56) References Cited

U.S. PATENT DOCUMENTS

| | | |
|---|---|---|
| 2008/0234785 A1 | 9/2008 | Nakayama et al. |
| 2008/0243014 A1 | 10/2008 | Moussavi et al. |
| 2008/0269625 A1* | 10/2008 | Halperin ............ A61B 5/746 |
| | | 600/534 |
| 2008/0275348 A1 | 11/2008 | Catt et al. |
| 2008/0275349 A1 | 11/2008 | Halperin et al. |
| 2008/0289637 A1 | 11/2008 | Wyss |
| 2008/0319277 A1 | 12/2008 | Bradley |
| 2009/0030767 A1 | 1/2009 | Morris et al. |
| 2009/0048540 A1 | 2/2009 | Otto et al. |
| 2009/0069644 A1 | 3/2009 | Hsu et al. |
| 2009/0071810 A1 | 3/2009 | Hanson et al. |
| 2009/0082699 A1 | 3/2009 | Bang et al. |
| 2009/0094750 A1 | 4/2009 | Oguma et al. |
| 2009/0105785 A1 | 4/2009 | Wei et al. |
| 2009/0121826 A1 | 5/2009 | Song et al. |
| 2009/0128487 A1 | 5/2009 | Langereis et al. |
| 2009/0143636 A1 | 6/2009 | Mullen et al. |
| 2009/0150217 A1 | 6/2009 | Luff |
| 2009/0177327 A1 | 7/2009 | Turner et al. |
| 2009/0203970 A1 | 8/2009 | Fukushima et al. |
| 2009/0203972 A1 | 8/2009 | Heneghan et al. |
| 2009/0207028 A1 | 8/2009 | Kubey et al. |
| 2009/0209839 A1 | 8/2009 | Ochs et al. |
| 2009/0227888 A1 | 9/2009 | Salmi et al. |
| 2009/0264789 A1 | 10/2009 | Molnar et al. |
| 2009/0320123 A1 | 12/2009 | Yu et al. |
| 2010/0010330 A1 | 1/2010 | Rankers et al. |
| 2010/0010565 A1* | 1/2010 | Lichtenstein ............ A61N 1/32 |
| | | 607/46 |
| 2010/0036211 A1 | 2/2010 | La et al. |
| 2010/0061596 A1 | 3/2010 | Mostafavi et al. |
| 2010/0075807 A1 | 3/2010 | Hwang et al. |
| 2010/0079291 A1 | 4/2010 | Kroll et al. |
| 2010/0079294 A1 | 4/2010 | Rai et al. |
| 2010/0083968 A1 | 4/2010 | Wondka et al. |
| 2010/0094139 A1 | 4/2010 | Brauers et al. |
| 2010/0094148 A1 | 4/2010 | Bauer et al. |
| 2010/0100004 A1 | 4/2010 | Van Someren |
| 2010/0102971 A1 | 4/2010 | Virtanen et al. |
| 2010/0152543 A1 | 6/2010 | Heneghan et al. |
| 2010/0152546 A1 | 6/2010 | Behan et al. |
| 2010/0217146 A1 | 8/2010 | Osvath |
| 2010/0256512 A1 | 10/2010 | Sullivan |
| 2010/0283618 A1 | 11/2010 | Wolfe et al. |
| 2010/0331145 A1 | 12/2010 | Lakovic et al. |
| 2011/0015467 A1 | 1/2011 | Dothie et al. |
| 2011/0015495 A1 | 1/2011 | Dothie et al. |
| 2011/0018720 A1 | 1/2011 | Rai et al. |
| 2011/0046498 A1 | 2/2011 | Klap et al. |
| 2011/0054279 A1 | 3/2011 | Reisfeld et al. |
| 2011/0058456 A1 | 3/2011 | Van et al. |
| 2011/0090226 A1 | 4/2011 | Sotos et al. |
| 2011/0105915 A1 | 5/2011 | Bauer et al. |
| 2011/0137836 A1 | 6/2011 | Kuriyama et al. |
| 2011/0160619 A1 | 6/2011 | Gabara |
| 2011/0190594 A1 | 8/2011 | Heit et al. |
| 2011/0199218 A1 | 8/2011 | Caldwell et al. |
| 2011/0230790 A1 | 9/2011 | Kozlov |
| 2011/0245633 A1 | 10/2011 | Goldberg et al. |
| 2011/0295083 A1 | 12/2011 | Doelling et al. |
| 2011/0302720 A1 | 12/2011 | Yakam et al. |
| 2011/0304240 A1 | 12/2011 | Meitav et al. |
| 2012/0004749 A1 | 1/2012 | Abeyratne et al. |
| 2012/0083715 A1 | 4/2012 | Yuen et al. |
| 2012/0232414 A1 | 9/2012 | Mollicone et al. |
| 2012/0243379 A1 | 9/2012 | Balli |
| 2012/0253220 A1 | 10/2012 | Rai et al. |
| 2012/0296156 A1 | 11/2012 | Auphan |
| 2013/0012836 A1 | 1/2013 | Crespo et al. |
| 2013/0018284 A1 | 1/2013 | Kahn et al. |
| 2013/0023214 A1 | 1/2013 | Wang et al. |
| 2013/0053653 A1 | 2/2013 | Cuddihy et al. |
| 2013/0053656 A1 | 2/2013 | Mollicone et al. |
| 2013/0060306 A1 | 3/2013 | Colbauch |
| 2013/0144190 A1 | 6/2013 | Bruce et al. |
| 2013/0184601 A1 | 7/2013 | Zigel et al. |
| 2013/0197857 A1 | 8/2013 | Lu et al. |
| 2013/0204314 A1 | 8/2013 | Miller et al. |
| 2013/0208576 A1 | 8/2013 | Loree et al. |
| 2013/0283530 A1 | 10/2013 | Main et al. |
| 2013/0286793 A1 | 10/2013 | Umamoto |
| 2013/0289419 A1 | 10/2013 | Berezhnyy et al. |
| 2013/0300204 A1 | 11/2013 | Partovi |
| 2013/0310658 A1 | 11/2013 | Ricks et al. |
| 2013/0344465 A1 | 12/2013 | Dickinson et al. |
| 2014/0005502 A1 | 1/2014 | Klap et al. |
| 2014/0051938 A1 | 2/2014 | Goldstein et al. |
| 2014/0085077 A1 | 3/2014 | Luna et al. |
| 2014/0135955 A1 | 5/2014 | Burroughs |
| 2014/0171815 A1 | 6/2014 | Yang et al. |
| 2014/0200691 A1 | 7/2014 | Lee et al. |
| 2014/0207292 A1 | 7/2014 | Ramagem et al. |
| 2014/0218187 A1 | 8/2014 | Chun et al. |
| 2014/0219064 A1 | 8/2014 | Filipi et al. |
| 2014/0232558 A1 | 8/2014 | Park et al. |
| 2014/0256227 A1 | 9/2014 | Aoki et al. |
| 2014/0259417 A1 | 9/2014 | Nunn et al. |
| 2014/0259434 A1 | 9/2014 | Nunn et al. |
| 2014/0273858 A1 | 9/2014 | Panther et al. |
| 2014/0276227 A1 | 9/2014 | Perez |
| 2014/0288878 A1 | 9/2014 | Donaldson |
| 2014/0306833 A1 | 10/2014 | Ricci |
| 2014/0350351 A1 | 11/2014 | Halperin et al. |
| 2014/0371635 A1 | 12/2014 | Shinar et al. |
| 2015/0015399 A1 | 1/2015 | Gleckler et al. |
| 2015/0068069 A1 | 3/2015 | Tran et al. |
| 2015/0073283 A1 | 3/2015 | Van et al. |
| 2015/0085622 A1 | 3/2015 | Carreel et al. |
| 2015/0094544 A1 | 4/2015 | Spolin et al. |
| 2015/0098309 A1 | 4/2015 | Adams et al. |
| 2015/0101870 A1 | 4/2015 | Gough et al. |
| 2015/0136146 A1 | 5/2015 | Hood et al. |
| 2015/0141852 A1 | 5/2015 | Dusanter et al. |
| 2015/0148621 A1 | 5/2015 | Sier |
| 2015/0148871 A1 | 5/2015 | Maxik et al. |
| 2015/0164238 A1 | 6/2015 | Benson et al. |
| 2015/0164409 A1 | 6/2015 | Benson et al. |
| 2015/0164438 A1 | 6/2015 | Halperin et al. |
| 2015/0164682 A1 | 6/2015 | Remmers et al. |
| 2015/0173671 A1 | 6/2015 | Paalasmaa et al. |
| 2015/0178362 A1 | 6/2015 | Wheeler |
| 2015/0190086 A1 | 7/2015 | Chan et al. |
| 2015/0220883 A1 | 8/2015 | Lingg et al. |
| 2015/0233598 A1 | 8/2015 | Shikii et al. |
| 2015/0238139 A1 | 8/2015 | Raskin et al. |
| 2015/0265903 A1 | 9/2015 | Kolen et al. |
| 2015/0289802 A1 | 10/2015 | Thomas et al. |
| 2015/0320588 A1 | 11/2015 | Connor |
| 2015/0333950 A1* | 11/2015 | Johansson ............ H03M 1/1215 |
| | | 375/349 |
| 2015/0346824 A1* | 12/2015 | Chen ..................... H04N 5/144 |
| | | 345/156 |
| 2015/0351694 A1 | 12/2015 | Shimizu et al. |
| 2016/0015315 A1 | 1/2016 | Auphan et al. |
| 2016/0045035 A1 | 2/2016 | Van Erlach |
| 2016/0217672 A1 | 7/2016 | Yoon et al. |
| 2016/0262693 A1 | 9/2016 | Sheon |
| 2016/0287869 A1* | 10/2016 | Errico ..................... H04M 1/21 |
| 2017/0003666 A1 | 1/2017 | Nunn et al. |
| 2017/0020756 A1 | 1/2017 | Hillenbrand et al. |
| 2017/0188938 A1 | 7/2017 | Toh et al. |
| 2018/0049701 A1 | 2/2018 | Raisanen |
| 2018/0103770 A1 | 4/2018 | Nava et al. |
| 2018/0338725 A1 | 11/2018 | Shan et al. |
| 2019/0021675 A1 | 1/2019 | Gehrke et al. |
| 2019/0044380 A1 | 2/2019 | Lausch et al. |
| 2019/0132570 A1 | 5/2019 | Chen et al. |
| 2019/0156296 A1 | 5/2019 | Lu et al. |

(56) References Cited

U.S. PATENT DOCUMENTS

| | | | |
|---|---|---|---|
| 2019/0190992 | A1 | 6/2019 | Warrick |
| 2019/0201270 | A1 | 7/2019 | Sayadi et al. |

FOREIGN PATENT DOCUMENTS

| | | | |
|---|---|---|---|
| CH | 668349 | A | 12/1988 |
| CH | 697528 | B1 | 11/2008 |
| DE | 4101471 | A1 | 7/1992 |
| DE | 19642316 | A1 | 4/1998 |
| EP | 1139187 | A2 | 10/2001 |
| JP | 08-160172 | A | 6/1996 |
| JP | 2007-132581 | A | 5/2007 |
| KR | 10-2009-0085403 | A | 8/2009 |
| KR | 10-2010-0022217 | A | 3/2010 |
| WO | 93/02731 | A1 | 2/1993 |
| WO | 2008/038288 | A2 | 4/2008 |
| WO | 2009/099292 | A2 | 8/2009 |
| WO | 2011/141840 | A1 | 11/2011 |

OTHER PUBLICATIONS

Acligraphy, From Wikipedia, the free encyclopedia, downloaded at: http://en.wikipedia.org/wiki/Actigraphy on Apr. 24, 2014, 4 pages.
Advisory Action, U.S. Appl. No. 16/601,561, Feb. 1, 2022, 3 pages.
Campbell, Appleinsider, "Apple buys sleep tracking firm Beddit" May 9, 2017. Retrieved from https://appleinsider.com/articles/17/05/09/apple-buys-sleep-tracking-firm-beddit (Year: 2017).
Crist, CNET "Samsung introduces SleepSense" Sep. 3, 2015. Retrieved from https://www.cnet.com/reviews/samsung-sleepsense-preview (Year: 2015).
Daniel et al., "Activity Characterization from Actimetry Sensor Data for Sleep Disorders Diagnosis", Sep. 2008, 10 pages.
Desai, Rajiv, "The Sleep", Mar. 17, 2011, Educational Blog, 82 pages.
Final Office Action, U.S. Appl. No. 16/601,561, Nov. 5, 2021, 21 pages.
Fitbit Product Manual, "Fitbit Product Manual", available online at <http://www.filtbit.com/manual>, Mar. 29, 2010, pp. 1-20.
Haughton Mifflin, "Estimate", The American Heritage dictionary of the English language (5th ed.), Jul. 24, 2017, 2 pages.
How BodyMedia FIT Works, <http://www.bodymedia.com/Shop/Learn-More/How-it-works>, accessed Jun. 17, 2011, 2 pages.
Internet Archive, Withings "Sleep Tracking Mat" Nov. 22, 2018. Retrieved from https://web.archive.org/web/20181122024547/https://www.withings.com/us/en/sleep (Year: 2018).
Jaines, Kira, "Music to Help You Fall Asleep," <http://www.livestrong.com/article/119802-music-fall-sleep/>, May 10, 2010, 2 pages.
JETLOG Reviewers Guide, <http://www.jetlog.com/fileadmin/Presse_us/24x7ReviewersGuide.pdf>, 2009, 5 pages.
Leeds, Joshua, "Sound-Remedies.com: Sonic Solutions for Health, Learning & Productivity," <http://www.sound-remedies.com/ammusforslee.html>, Accessed May 23, 2013, 2 pages.
Lichstein, et al., "Actigraphy Validation with Insomnia", SLEEP, vol. 29, No. 2, 2006, pp. 232-239.
Liden et al., "Characterization and Implications of the Sensors Incorporated into the SenseWear(TM) Armband for Energy Expenditure and Activity Detection", 2011, 7 pages.
Mattila et al., "A Concept for Personal Wellness Management Based on Activity Monitoring," Pervasive Computing Technologies for Healthcare, 2008.
Notice of Allowance, U.S. Appl. No. 16/601,561, Jun. 17, 2022, 13 pages.
Patel, et al., Validation of Basis Science Advanced Sleep Analysis, Estimation of Sleep Stages and Sleep Duration, Basis Science, San Francisco, CA, Jan. 2014, 6 pages.
Pires, P. D. C. Activity Characterization from Actimetry Sensor Data for Sleep Disorders Diagnosis, Universidade T ecnica de Lisboa, Sep. 2008, 10 pages.
Pollak et al., "How Accurately Does Wrist Actigraphy Identify the States of Sleep and Wakefulness?", Sleep, vol. 24, No. 8, 2001, pp. 957-965.
Power Nap, <en.wikipedia.org/wiki/Power.sub.-nap>, Last Modified Sep. 20, 2012, 4 pages.
PowerNap, "iPhone App", available online at <http://forums.precentral.net/webos-apps-software/223091-my-second-app-powernap-out-app-catalog-nap-timer.html>, Jan. 6, 2010, 10 pages.
Rechtschaffen et al., Manual of Standardized Terminology, Techniques and Scoring System for Sleep Stages of Human Subjects, 1968, 57 pages.
Sara Mednick, <en.wikipedia.org/wiki/Sara.sub.-Mednick>, Last Modified Sep. 12, 2012, 2 pages.
Schulz et al. "Phase shift in the REM sleep rhythm." Pflugers Arch. 358, 1975, 10 pages.
Schulz et al. "The REM-NREM sleep cycle: Renewal Process or Periodically Driven Process?." Sleep, 1980, pp. 319-328.
Sleep Debt, <en.wikipedia.org/wiki/Sleep.sub.-debt>, Last Modified Aug. 25, 2012, 3 pages.
Sleep Inertia, <en.wikipedia.org/wiki/Sleep_inertia>, Last Modified Sep. 12, 2012, 2 pages.
Sleep, <en.wikipedia.org/wiki/Sleep.sub.-stages#Physiology>, Last Modified Oct. 5, 2012, 21 pages.
Slow Wave Sleep, <en.wikipedia.org/wiki/Slow-wave.sub.-sleep>, Last Modified Jul. 22, 2012, 4 pages.
Sunseri et al., "The SenseWear (TM) Armband as a Sleep Detection Device," available online at <http://sensewear.bodymedia.com/SenseWear-Sludies/SW-Whilepapers/The-SenseWear-armband-as-a-Sleep-Delection-Device>, 2005, 9 pages.
Wikipedia, "David.sub Dinges", available online at <en.wikipedia.org/wiki/David.sub_Dinges>, Sep. 12, 2012, 2 pages.
Yassourdidis et al. "Modelling and Exploring Human Sleep with Event History Analysis." Journal of Sleep Research, 1999, pp. 25-36.
Ding, F., et al., "Polysomnographic validation of an under-mattress monitoring device in estimating sleep architecture and obstructive sleep apnea in adults," Sleep Medicine, vol. 96, Apr. 2022, pp. 20-27.
Choudhary, S. and Choudhary, S, Sleep Effects on Breathing and Respiratory Diseases, Review Article, Oct.-Dec. 2009, 117-122 pages, vol. 26, Issue 4, Department of Pulmonary Medicine, Sleep Medicine, Critical Care, Shree Ramjevan Choudhary Memorial Hospital and Research Centre, Nagpur—02, India, 6 pages.
Verbraecken, J, Applications of Evolving Technologies in Sleep Medicine, Article, Dec. 2013, 443-455 pages, vol. 9, No. 6, Dept of Pulmonary Medicine and Multidisciplinary Sleep Disorders Centre, Antwerp University Hospital, Antwerp, Belgium, 14 pages.

* cited by examiner

HARDWARE SENSOR SYSTEM FOR IMPROVED SLEEP DETECTION

RELATED APPLICATION

The present application is a continuation of U.S. patent application Ser. No. 16/601,561, filed Oct. 14, 2019, issuing as U.S. Pat. No. 11,471,097 on Oct. 18, 2022, which application claims priority to U.S. Provisional Patent Application 62/745,976 filed on Oct. 15, 2018. The present application also claims priority to U.S. Provisional Patent Application No. 62/745,978 (8689P232Z) and U.S. Provisional Application No. 62/745,984 (8689P233Z) both filed on Oct. 15, 2019 and incorporates all three of those applications by reference in their entirety.

FIELD

The present invention relates to sleep sensors, and more particularly to an improved sleep detection system including sensor hardware.

BACKGROUND

An average person spends about one-third of his or her life asleep. Sleep is the time our bodies undergo repair and detoxification. Research has shown that poor sleep patterns is an indication of and often directly correlated to poor health. Proper, restful and effective sleep has a profound effect on our mental, emotional and physical well-being.

Every person has a unique circadian rhythm that, without manipulation, will cause the person to consistently go to sleep around a certain time and wake up around a certain time. For most people, a typical night's sleep is comprised of five different sleep cycles, each lasting about 90 minutes. The first four stages of each cycle are often regarded as quiet sleep or non-rapid eye movement (NREM). The final stage is often denoted by and referred to as rapid eye movement (REM). REM sleep is thought to help consolidate memory and emotion. REM sleep is also the time when blood flow rises sharply in several areas of the brain that are linked to processing memories and emotional experiences. During REM sleep, areas of the brain associated with complex reasoning and language experience blood flow declines, whereas areas of the brain associated with processing memories and emotional experiences exhibit increased blood flow.

Therefore, it is useful for everyone to know more about how well they sleep.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

A sleep monitoring system is described. The system includes analog and digital elements, which collect data from a sleeper and provide it for processing and analysis to a server system. In one embodiment, the sleep monitoring system includes a sensor which is designed to be placed under a user's mattress or mattress topper, or in a user's bedframe. In one embodiment, this sensor collects movement data, and sends it through an insulated cable to a receiver. In another embodiment, the data may be sent wirelessly. The receiver, which in one embodiment is positioned in proximity to the bed, receives the insulated cable or wireless signal, and converts the data to a digital signal. In one embodiment, the digital signal is uploaded to the server for further processing and analysis. The server analyzes the sleep data, and can be used to set the receiver's operation, as well as control the user's sleep environment, in one embodiment.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized, and that logical, mechanical, electrical, functional and other changes may be made without departing from the scope of the present invention. The following detailed description is, therefore, not to be taken in a limiting sense, and the scope of the present invention is defined only by the appended claims.

Figure 1:
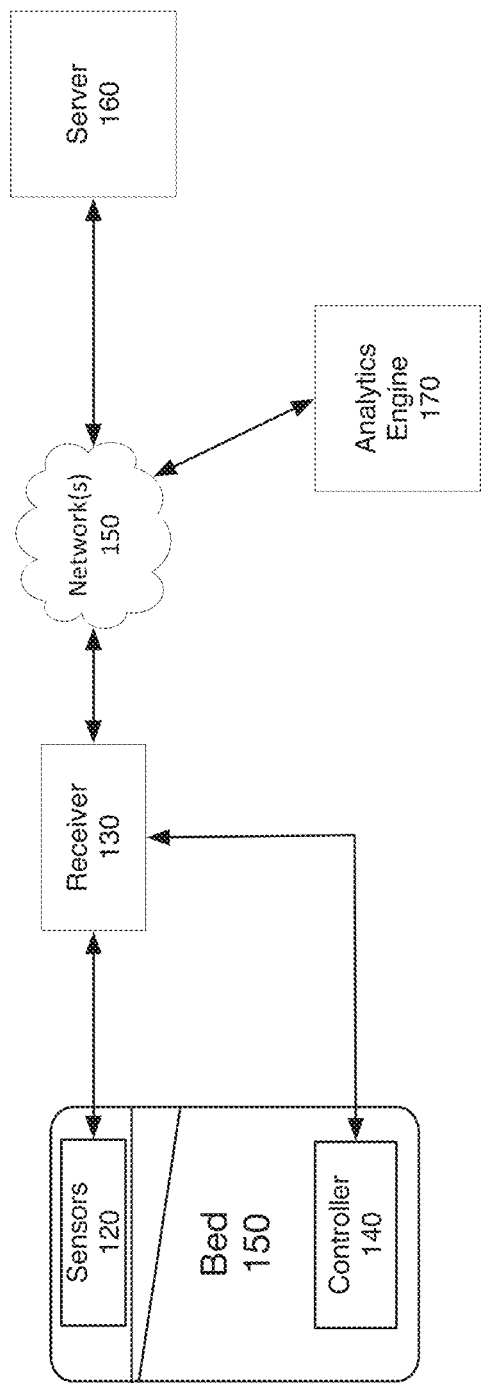
FIG. 1 is block diagram of one embodiment of a system in which the sensor system may be implemented.

FIG. 1 is block diagram of one embodiment of a system in which the sensor system may be implemented. The system includes a sleep analytics system 100 including sensors 120, receiver 130, server 160, and analytics engine 170. In one embodiment, the client portion of the sleep analytics system 100 is located in a user's home includes the sensors 120 and receiver 130.

In one embodiment, the receiver 130 is coupled to sensors 120 via a cable. In another embodiment the connection may be wireless, such as low power Bluetooth (BLE), Wi-Fi, or another type of wireless connection. In one embodiment, receiver 130 also may be coupled to a controller 140, which controls bed 150. In one embodiment, this connection is a wired connection. Alternatively, it may be a wireless connection.

In one embodiment, the sensors 120 may include one or more sensors positioned in bed 150 which are used to measure the user's sleep. In one embodiment, sensors 120 may include sensors which are not in bed 150 but positioned in the room in which the bed 150 is located. In one embodiment, one or more these additional sensors may be built into receiver 130. In one embodiment, there may be external sensors which may be coupled to receiver 130 either via wires or wirelessly. The receiver 130 collects data from the one or more sensors, for transmission to the server 160.

In one embodiment, the receiver 130 is coupled to the server 160 via a network 150. The server portion includes server 160 and analytics engine 170, which in one embodiment are located off-site, removed from the user. In another embodiment, the server may be a local system, such as a computer system running an application. The network 150 may be the Internet, and the receiver 130 may send data to the server via a wireless network, such as Wi-Fi or the cellular network. In one embodiment, server 160 and analytics engine 170 may be on the same physical device. In one embodiment, server and/or analytics engine 170 may include a plurality of devices. In one embodiment, one or both of the server 170 and the analytics engine 170 may be using cloud computing and may be implemented as a distributed system.

Figure 2:
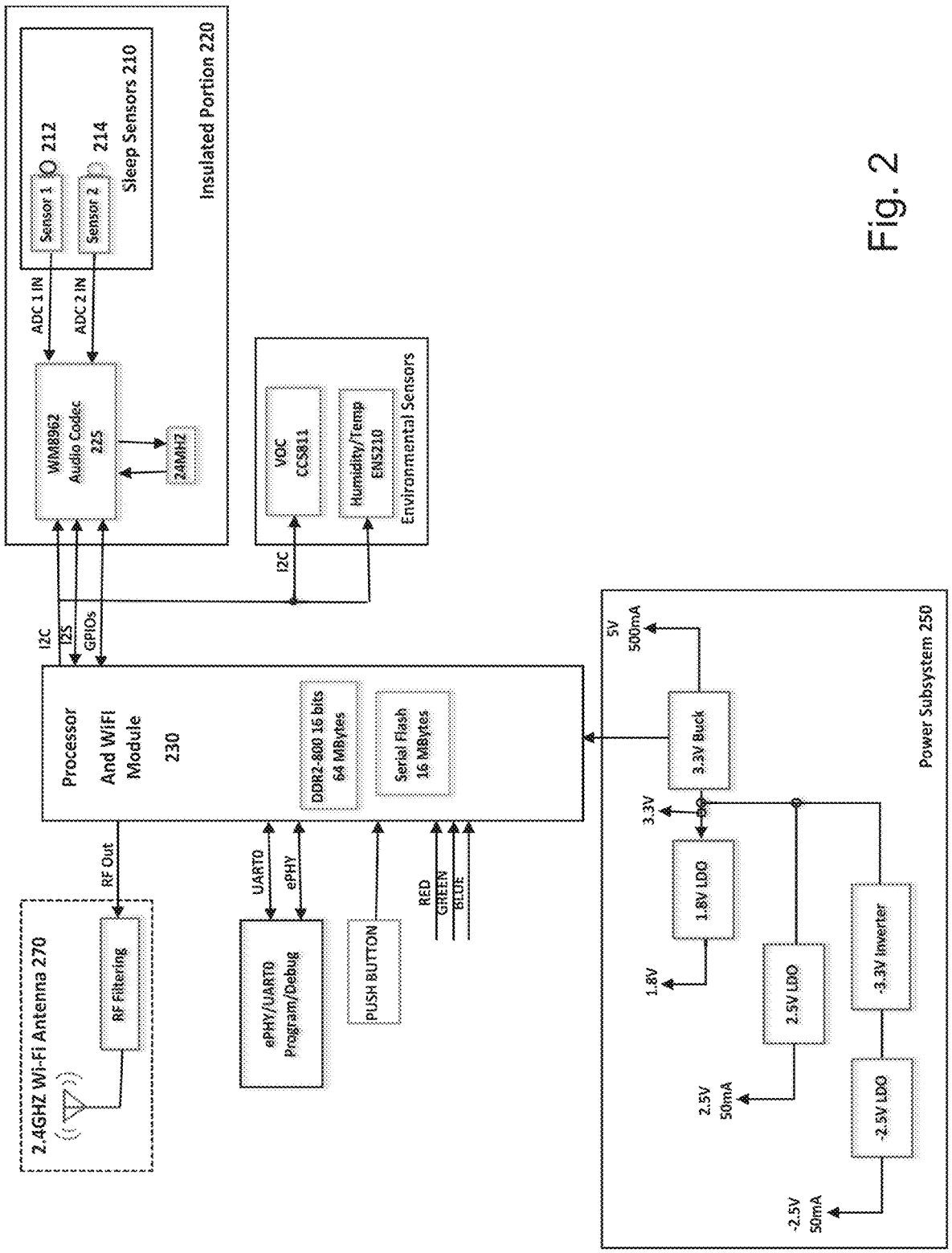
FIG. 2 is a block diagram of one embodiment of the sensor and receiver portion of the sensor system.

FIG. 2 is a block diagram of one embodiment of the sensor and receiver portion of the sensor system. In one embodiment, sleep sensors 210 include two sensors 212, 214, which are designed to be placed underneath a mattress, mattress topper, or mattress cover. In one embodiment, the sensors are piezoelectric sensors positioned on a hard foam surface to provide compressibility and support. In one embodiment, the sensors are coupled to an audio codec 225 to encode the data, for transmission to the server. By using audio codec, the data can be encoded in a way that provides 100% accuracy and a reduction in data size. In one embodiment, the receiver further includes additional environmental sensors 225. In one embodiment, the environmental sensors 225 may include a humidity and temperature sensor and a volatile organic compounds (VOC) sensor. Other sensors may also be included in the receiver.

In one embodiment, he encoded data from the sleep sensors 210 and the data from the environmental sensors 225 (which may also be encoded in some embodiments) are passed to a processor and Wi-Fi module 230. The processor and Wi-Fi module 230 sends the data to the server via a Wi-Fi connection 270. In another embodiment, the processor and Wi-Fi module 230 may be replaced by a separate processor and network access element. The Wi-Fi module may be replaced by a mobile network chip. In one embodiment, the processor and Wi-Fi module 230 includes a random access memory, such as DDR2, to buffer the data from the sensors, prior to transmission. In one embodiment, a flash memory may store the code for the processor 230.

In one embodiment, power subsystem 250 provides power to the processor 230, codec 225, and environmental sensors. In one embodiment, the power subsystem 250 provides a 3.3V power to the processor 230. In one embodiment, the power subsystem 250 also provides 1.8V to the audio codec 225, or other elements of the system. In one embodiment, the sleep sensors 210 provide their data as charge data between 2.5V and −2.5V. Thus, in one embodiment, the power subsystem handles voltages between −2.5V and 5V.

Figure 3:
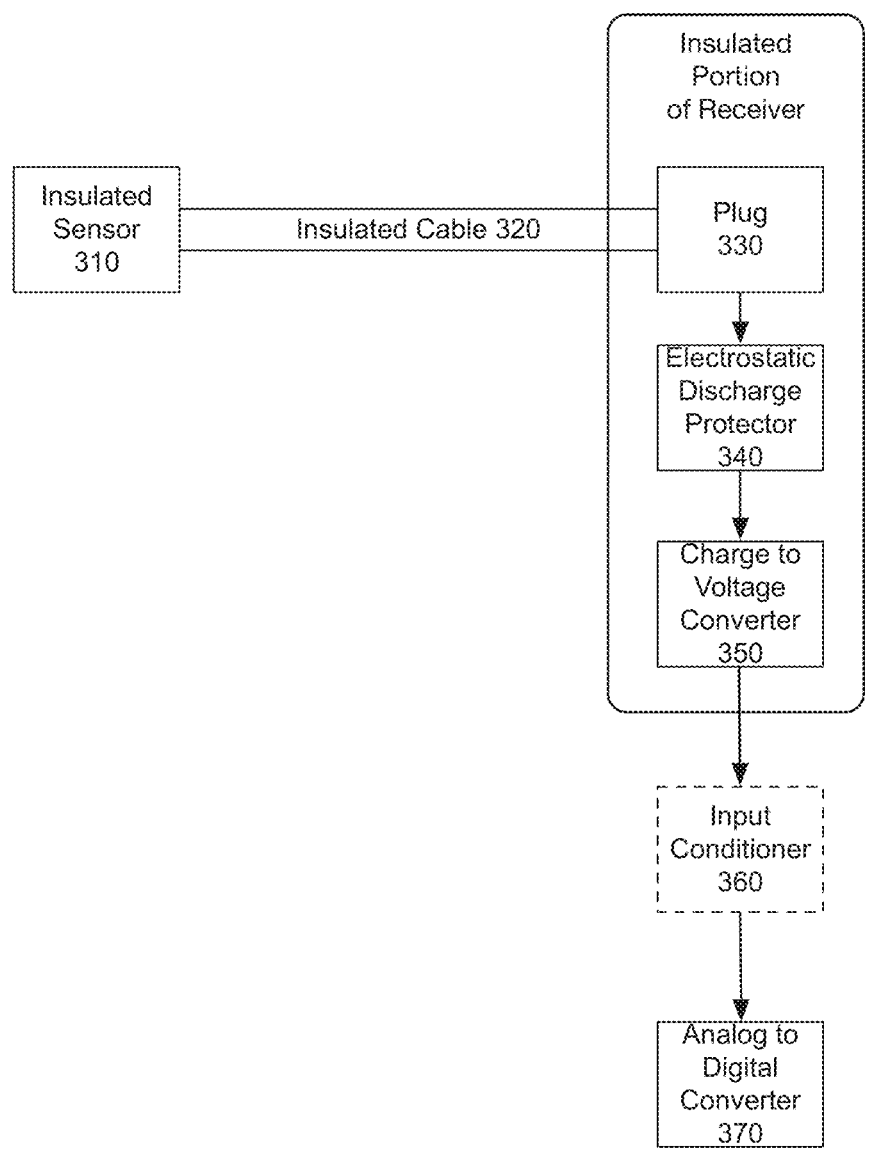
FIG. 3 is a block diagram of one embodiment of the first portion of the receiver and the A-to-D converter.

FIG. 3 is a block diagram of one embodiment of the first portion of the receiver and the A-to-D converter. In one embodiment, the system includes an insulated sensor 310. The insulated sensor is a piezo sensor, which is sensitive to movement. The sensor 310 itself is insulated, to ensure that it is not impacted by stray signals. Because the sensor 310 provides data as a voltage level, any noise impacting the sensor 310 may overwhelm the real data. In one embodiment, a ground connection is provided to the sensor 310 to provide insulation. The sensor 310 is coupled to the receiver 300 via cable 320, in one embodiment. In one embodiment, the cable 320 is a grounded cable. In one embodiment, the cable 320 is a custom shielded cable with two conductors.

The cable 320 connects to a plug 330 in receiver. In one embodiment, the plug is an insulated plug, to shield the data from the sensor from noise. In one embodiment, an electrostatic discharge protector (EDS) 340 is coupled to the line as well. A charge to voltage converter 350 converts the output of the sensors 310, which is charge data, into a voltage. The plug 330, EDS protector 340, and charge to voltage converter 350 all are on an insulated portion 220 of the receiver. In one embodiment, a custom metal enclosure provides the insulation. In one embodiment, the custom metal enclosure is grounded. In one embodiment, the receiver utilizes a three-prong plug, to request a grounded outlet. In one embodiment, the receiver verifies that the wall connection provides a proper ground. In one embodiment, the user may be alerted if the receiver is plugged into an ungrounded outlet. However, in one embodiment, the metal enclosure provides protection/insulation even when not properly grounded.

The output of the charge to voltage converter 350 is passed to an input conditioner, in one embodiment. The input conditioner 360 adjusts the voltage range of the signal. The voltage is then passed to an analog to digital converter 370, in one embodiment. This converts the analog sensor data into a digital signal. The output of the analog to digital converter 370 is encoded and sent to the server for analysis. In one embodiment, the digital signal is encoded to ensure error correction. The signal may also be compressed.

For simplicity this figure, and others, illustrate a single sensor and connection. In one embodiment, the system may include two sensors when configured to detect two sleepers. In one embodiment, the system may include more than two sensors. When additional sensors are used, they may be separately handled. In one embodiment, each sensor has a separate and substantially identical path. In another embodiment, multiple sensors may send their data to the receive through a shared path.

Figure 4:
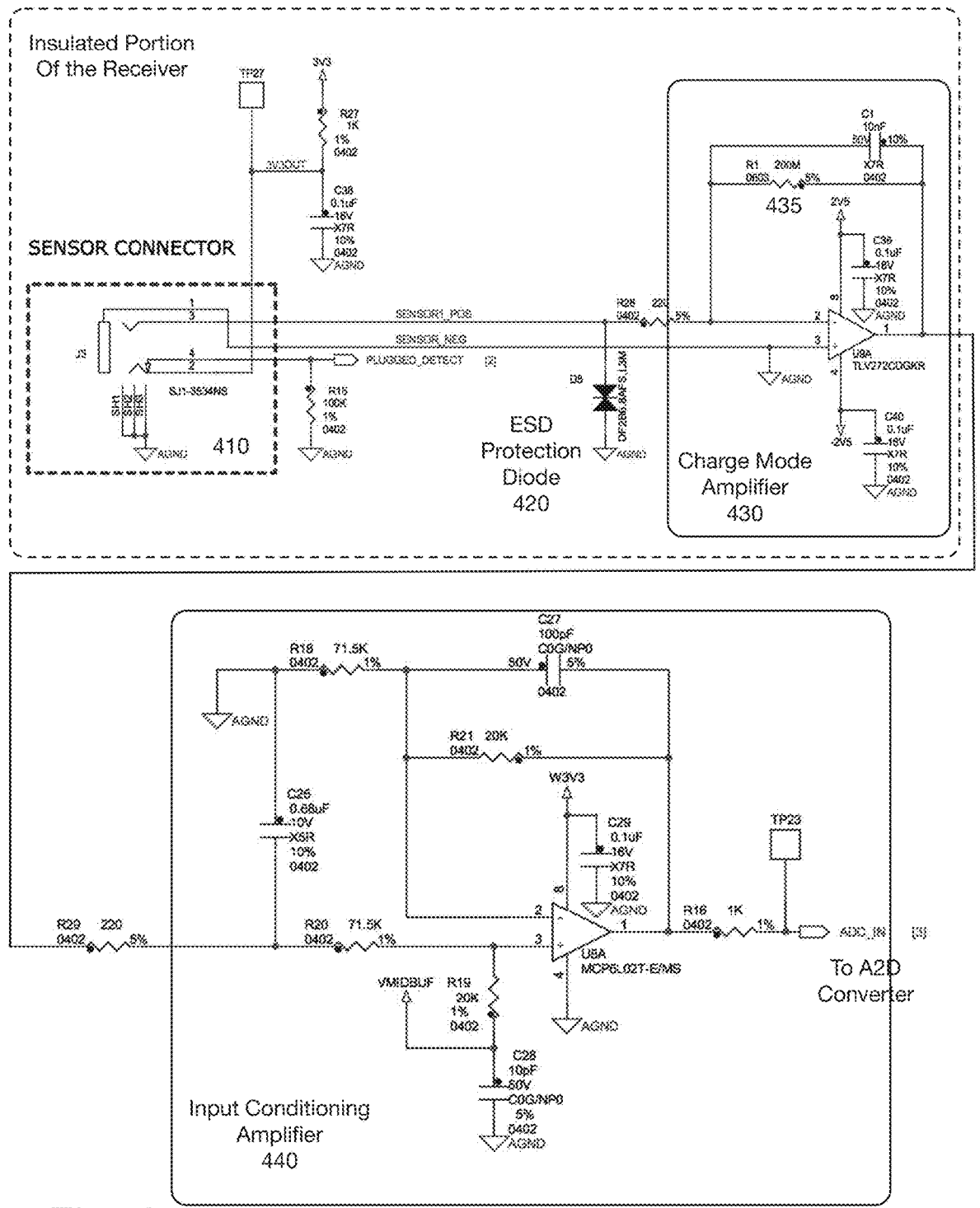
FIG. 4 is a circuit diagram of one embodiment of the first portion of the receiver.

FIG. 4 is a circuit diagram of one embodiment of the first portion of the receiver. The receiver includes the sensor connector 410 to which the cable is coupled. ESD protection diode 420 is tied to ground and protects against electrostatic discharge.

The charge mode amplifier 430 provides a charge to voltage conversion for the signal from the sensors. The charge mode amplifier is an op-amp with a negative feedback capacitor and a large resistor 435, converting the charge signal to a voltage output.

The voltage output from the charge mode amplifier 430 is passed to an input conditioning amplifier 440. The input conditioning amplifier is 440 an op-amp that adjusts the voltage range of the signal, for the analog-to-digital converter. In one embodiment, the input to the input conditioning amplifier a voltage value between −2.5V and 2.5V and adjusts it to 0V to 1.8V. In one embodiment, this element may be skipped if the Analog-to-Digital converter can handle the voltage range output by the charge mode amplifier 430.

Figure 5:
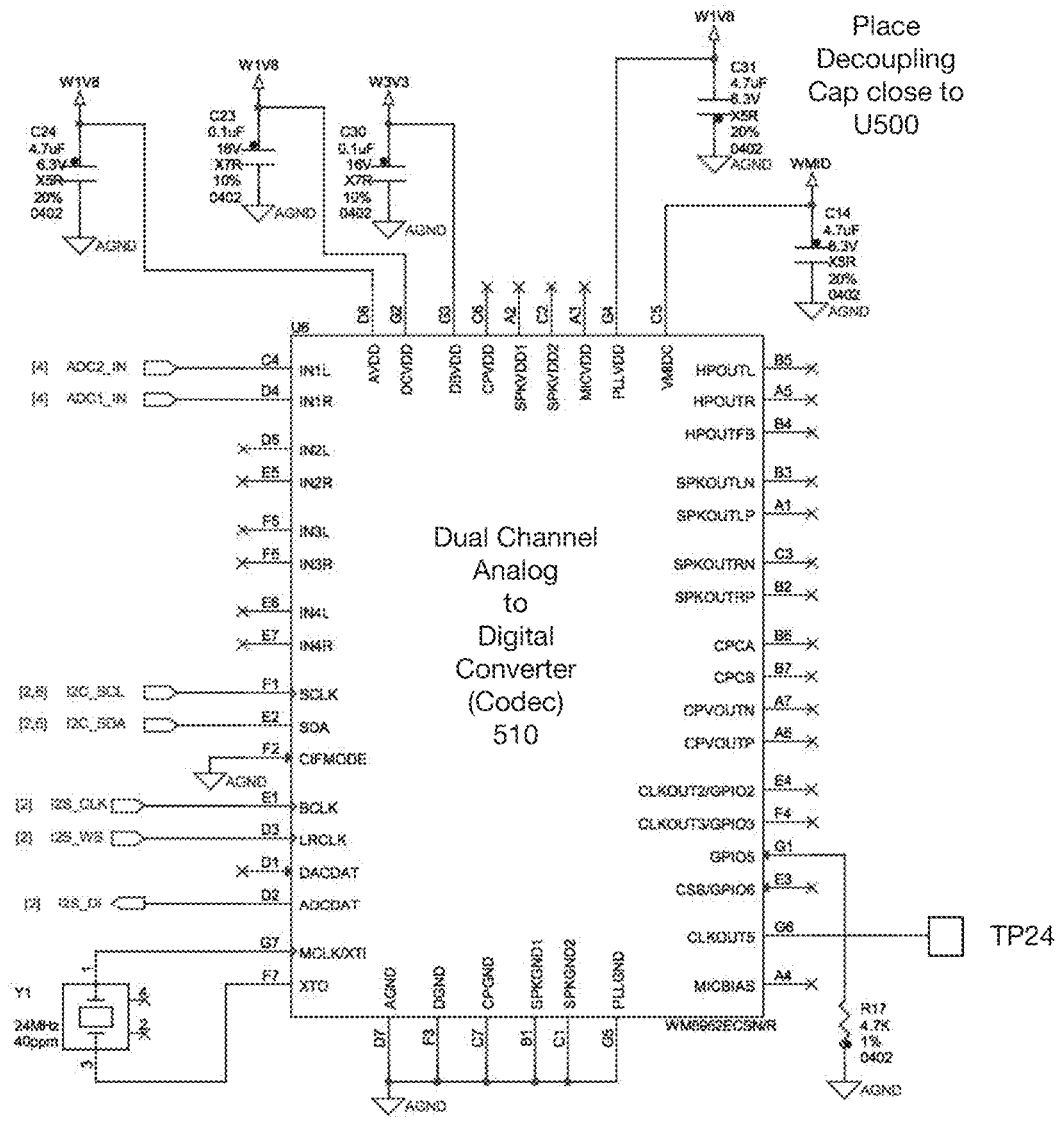
FIG. 5 is a circuit diagram of one embodiment of the A-to-D converter.
Figure 5:
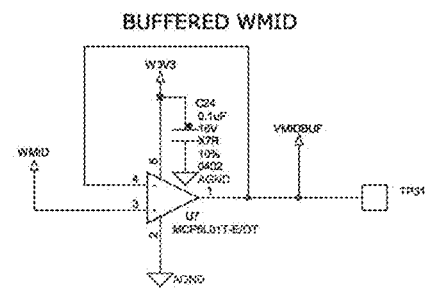

FIG. 5 is a circuit diagram of one embodiment of the A-to-D converter. In one embodiment, for simplicity and to ensure that the two signals are processed in a synchronized manner, the A-to-D converter 510 is an Audio CODEC, which provides concurrent sampling of two channels, at 24 bits. This maintains time alignment between data from the two sensors. Of course, another type of analog-to-digital converter may be used. In one embodiment, the A-to-D converter used should provide at least two channels, and at least an 18-bit rate sampling. This is the last portion of the receive which is analog. The output of the A-to-D converter is digital and is passed to the digital portion of the receiver. In one embodiment, the analog portion of the receiver and the digital portion are on separate substrates.

Figure 6:
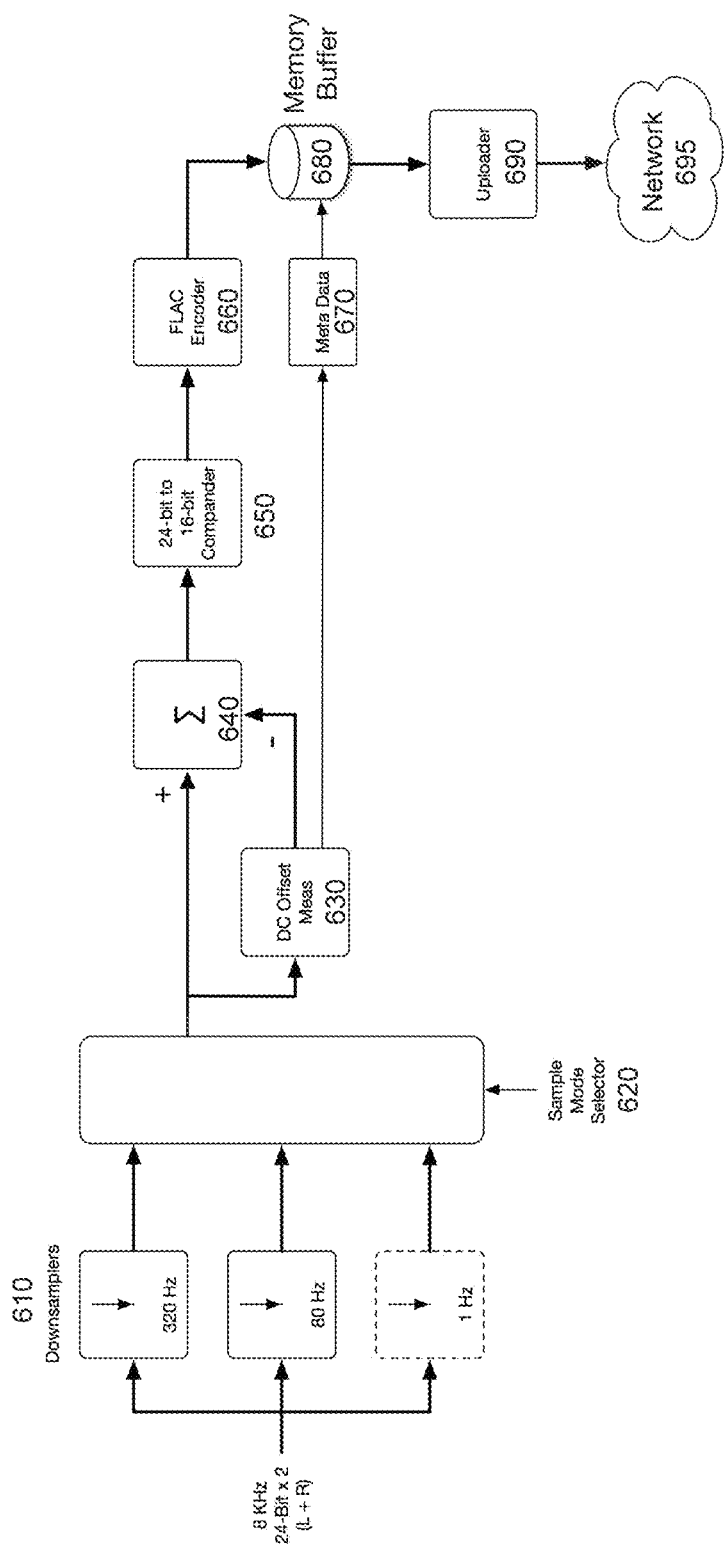
FIG. 6 is a block diagram of one embodiment of the digital portion of the receiver.

FIG. 6 is a block diagram of one embodiment of the digital portion of the receiver. The data from the A-to-D converter in one embodiment is 24-bit two channel data.

This is input into a downsampler 610, in one embodiment. In one embodiment, the receiver selects which downsampler to utilize. In one embodiment, the server controls the receiver's selection. In one embodiment, the selection is based on the data received and analyzed by the server.

The reason for sample rate selection is to optimize the upload based on a current state of the sleep monitor. In one embodiment, the sleep monitor states may include: not in use (no one on bed), in use for limited analysis, and in full use. For example, in one embodiment, if no one is on the bed, the rate can be downsampled to a lowest sample rate, for example between 0.5 and 5 Hz. In one embodiment, the lowest sample rate is 1-Hz. If only sleep-states and HR/BR measurements are being utilized, the sample rate can be reduced to a mid-range frequency, for example 30 to 100 Hz. In one embodiment, the midrange frequency is 80 Hz. 80-Hz. Whereas, if sleep states, HR/BR, snore detection, respiratory events, HRV, etc., are being measured, a higher rate, for example 100 Hz to 500 Hz may be used. In one embodiment, the higher rate is a 320-Hz rate. In one embodiment, the sample mode selector 620 determines the sampling rate. In one embodiment, software services running on the cloud determine and remotely set the sample rate selection 620.

In one embodiment, a DC offset measurement 630 allows DC offset removal 640 (shown as an element labeled with a Greek letter sigma). The DC offset removal 620 is to allow the compander 650 to be as efficient as possible. In one embodiment, the DC offset is recorded with the FLAC data, as meta data 670, so that the server can re-add the DC offset after expanding (un-companding) the data.

The compander 650 is used to reduce the uploaded data size, removing non-essential values from the data stream.

The compressed data is then encoded, in one embodiment. In one embodiment, free lossless audio codec (FLAC) encoder 660 is used to encode the data. In another embodiment, another lossless compression algorithm may be used, such as MPEG-4 ALS. In other embodiments, alternative encoding may be used. In one embodiment a lossy compression, such as a variant of MP3 may be used. In such an embodiment, the compression may be tuned for the data content so that the loss is minimal.

The FLAC data is stored in a memory 680 and then uploaded by uploader 690, to server via a network 695. In one embodiment, the uploader 690 uploads bursts of data. In one embodiment, the upload interval is specified by the cloud servers. In another embodiment, the uploader 690 uploads data when a certain amount of data is accumulated. This may result in slower uploads for data with a lower sample rate.

In one embodiment, the digital portion of the system runs in firmware on a processor.

Figure 7:
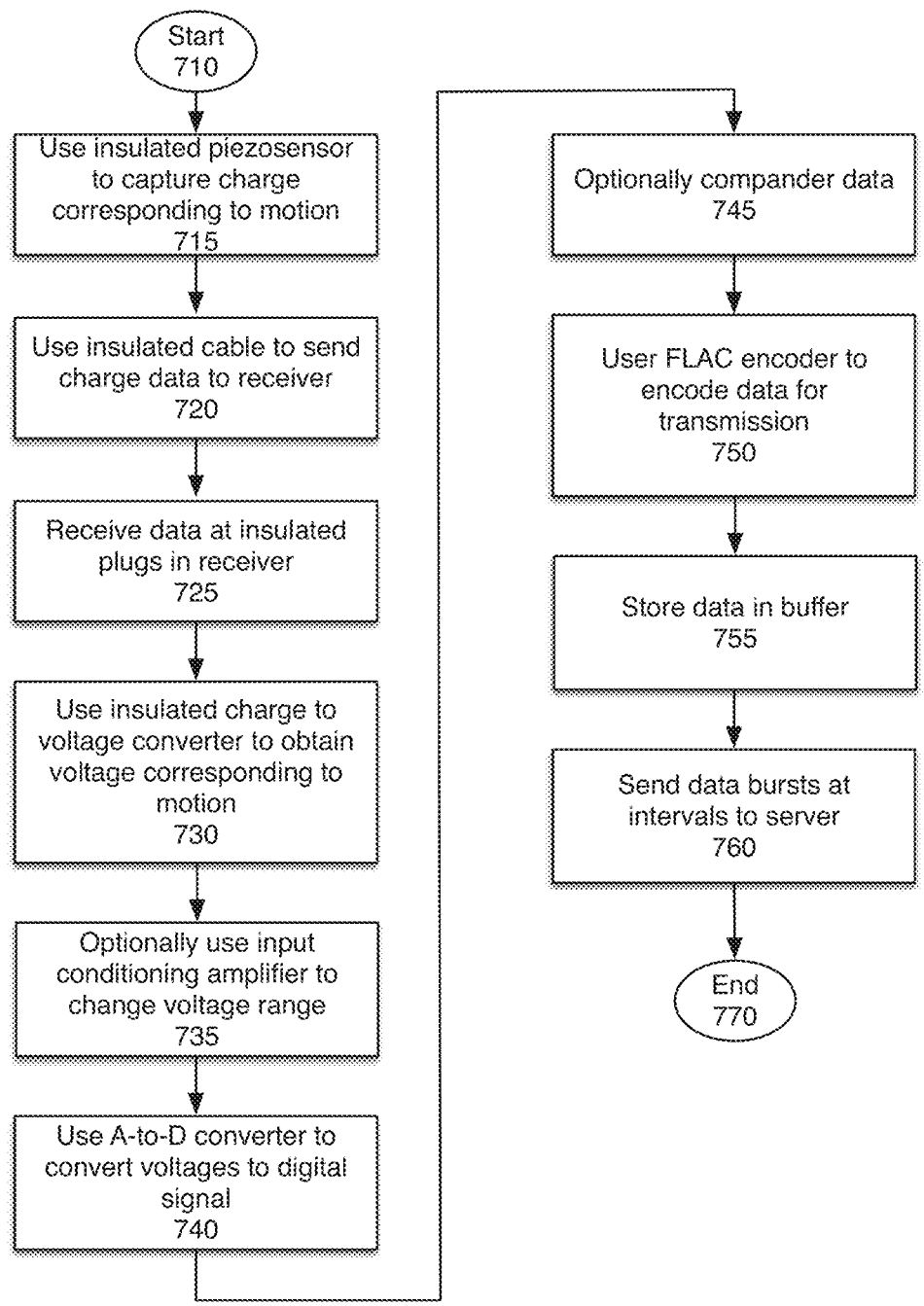
FIG. 7 is a flowchart of one embodiment of data collection through upload to the server.

FIG. 7 is a flowchart of one embodiment of data collection through upload to the server. The process starts at block 710. At block 715, insulated piezoelectric sensors are used to capture charge corresponding to motion. This data recording is sufficiently sensitive so that the data reflects not only body movements, but also the movement of the chest in breathing, as well as the movement of the rib cage in heart beats. The sensor is sensitive enough that it can record, and the AI-enabled system can identify, snoring based on the vibration of the user's throat, which is detected by the sensor.

The system, at block 720, uses an insulated cable to send the charge data to the receiver, in one embodiment. Because the data is very precise even a small amount of noise can reduce the precision sufficiently to create an issue. Therefore, the data from the time the sensor detects it, until it is converted to a voltage, is run through an insulated system.

The insulated cable connects the data to insulated plugs, where the data is received at block 725, in one embodiment.

A charge-to-voltage converter is used to obtain a voltage corresponding to the charge data, reflecting the motion sensed by the sensors, at block 730. Optionally, at block 735, a conditioning amplifier may be used to adjust the voltage range for the A-to-D converter.

At block 740, the A-to-D converter converts the voltages to a digital signal. In one embodiment, the insulation may extend to the A-to-D converter. In another embodiment, once the signal is converted to a voltage, the signal is more robust, and the path need no longer be fully insulated.

At block 745, the data is compandered, in one embodiment.

At block 750, the data is encoded for transmission. In one embodiment, the encoding uses a lossless encoding algorithm. In one embodiment, a FLAC encoding is used. In one embodiment, this allows the use of an audio CODEC for the encoding.

At block 755, in one embodiment the data is stored in buffer. In one embodiment, at block 760 the data is sent in bursts to the server. In another embodiment, the data may be sent continuously. In another embodiment, the data may be sent periodically. The process then ends at block 770.

Of course, though this is shown as a flowchart, in one embodiment it is implemented as an interrupt-driven system, such that the device state is changed when a state detection system identifies a change of the state. Additionally, the ordering of state checking is arbitrary.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A hardware sleep sensor system comprising:
   a sensor outputting sensor data corresponding to a motion;
   a converter to convert the sensor data to digital data;
   a downsampler configured to receive a down-sampling rate calculated based on a level of use of the sleep sensor system, wherein the level of use is one of: not in use level, limited analysis use level, and full use level;
   the downsampler further configured to down-sample an output of the converter using the down-sampling rate; and
   an uploader to upload the down-sampled digital data to a server for processing.

2. The system of claim 1, wherein the sensor is a piezo sensor outputting charge data corresponding to the motion.

3. The system of claim 1, further comprising:
   an insulated portion of the hardware sleep sensor system, the insulated portion including the sensor, a plug, and the converter.

4. The system of claim 3, wherein the insulated portion is insulated using a metal enclosure.

5. The system of claim 1, wherein the sensor is a piezo sensor, and the system further comprising:
   an electrostatic discharge protector coupled to a cable coupling the piezo sensor to a receiver.

6. The system of claim 1, wherein the converter is an analog-to-digital converter that a lossless algorithm to convert the sensor data to the digital data.

7. The system of claim 6, wherein the sensor data is charge data, and the system further comprising:
a charge to voltage converter to convert the charge data from the sensor into voltage data; and
the analog-to-digital converter to convert the voltage data to the digital data.

8. The system of claim 7, wherein the lossless algorithm is FLAC (free lossless compression), and the analog-to-digital converter is an audio codec.

9. The system of claim 1, comprising:
the sensor comprising two piezo sensors; and
a two-channel analog-to-digital converter to provide concurrent sampling of data from the two piezo sensors.

10. The system of claim 1, wherein:
the not in use level is defined as no user data being measured;
the limited analysis use level is defined as measuring: sleep state, heart rate and breathing rate; and
the full use level is defined as measuring the sleep state, the heart rate, and the breathing rate, and further measuring one or more of: snore detection, respiratory events, and heart rate variability.

11. The system of claim 1, wherein the down-sampling rate is 0.5 Hz to 5 Hz for the not in use level; is 30 Hz to 100 Hz for the limited analysis use level; and is 100 Hz to 500 Hz for the full use level.

12. The hardware sleep sensor system of claim 1, wherein:
the sensor outputting sensor data comprises two piezo sensors outputting charge data corresponding to the motion on a sleep surface;
an insulated portion of a receiver to receive the charge data from the two piezo sensors, the insulated portion coupled to the two piezo sensors via an insulated cable, and an insulated plug, the insulated cable including an electrostatic discharge protector;
the converter to convert sensor data comprises a charge to voltage converter for converting the charge data to voltage data, the charge to voltage converter on the insulated portion of the receiver, and a two-channel audio codec digital-to-analog converter to concurrently sample the charge data from the two piezo sensors, and to convert the voltage data to digital data using a lossless algorithm;
the downsampler further configured to down-sample an output of the converter using the down-sampling rate.

13. A method of monitoring a user with a sleep sensor system, the method comprising:
receiving sensor data from a sensor, the sensor data corresponding to a motion of the user;
converting the sensor data to digital data;
receiving a down-sampling rate calculated based on a level of use of the sleep sensor system, wherein the level of use is one of: not in use, limited analysis use, and full use;
down-sampling the digital data using the down-sampling rate; and
uploading the down-sampled digital data to a server for processing.

14. The method of claim 13, wherein the sensor data is received from a piezo sensor outputting charge data corresponding to the motion.

15. The method of claim 13, wherein a lossless algorithm is used to convert the sensor data to the digital data.

16. The method of claim 15, wherein the sensor data is charge data, and the method further comprises:
converting the charge data from the sensor into voltage data; and
converting the voltage data to the digital data.

17. The method of claim 15, wherein the lossless algorithm is an audio codec.

18. The method of claim 13, further comprising:
receiving sensor data an additional sensor; and
using a two-channel analog-to-digital converter to provide concurrent sampling of the data from the sensor and the additional sensor.

19. The method of claim 13, wherein:
the not in use level is defined as no user data being measured;
the limited analysis use level is defined as measuring: sleep state, heart rate and breathing rate; and
the full use level is defined as measuring the sleep state, the heart rate, and the breathing rate, and further measuring one or more of: snore detection, respiratory events, and heart rate variability.

20. The method of claim 13, wherein the down-sampling rate is 0.5 Hz to 5 Hz for the not in use level; is 30 Hz to 100 Hz for the limited analysis use level; and is 100 Hz to 500 Hz for the full use level.

21. A hardware sleep sensor system comprising:
two piezo sensors for outputting charge data corresponding to motion on a sleep surface;
an insulated portion of a receiver to receive the charge data from the two piezo sensors, the insulated portion coupled to the two piezo sensors via an insulated cable, and an insulated plug, the insulated cable including an electrostatic discharge protector;
a charge to voltage converter for converting the charge data to voltage data, the charge to voltage converter on the insulated portion of the receiver;
a two-channel audio codec digital-to-analog converter to concurrently sample the charge data from the two piezo sensors, and to convert the voltage data to digital data using a lossless algorithm;
a downsampler to down-sample an output of the digital-to-analog converter; and
an uploader to upload the down-sampled output to a server for processing.

* * * * *